United States Patent
Yamamoto et al.

(10) Patent No.: US 6,914,154 B2
(45) Date of Patent: Jul. 5, 2005

(54) PROCESS FOR PRODUCTION OF BIPHENYLTETRACARBOXYLIC ACID TETRAESTERS

(75) Inventors: Yasushi Yamamoto, Ube (JP); Tetsuro Tsuji, Ube (JP); Jun Haruta, Ube (JP); Kikuo Ataka, Ube (JP); Noboru Kakeya, Ube (JP)

(73) Assignee: Ube Industries, Ltd. (JP)

( * ) Notice: Subject to any disclaimer, the term of this patent is extended or adjusted under 35 U.S.C. 154(b) by 14 days.

(21) Appl. No.: 10/639,324

(22) Filed: Aug. 12, 2003

(65) Prior Publication Data

US 2004/0039222 A1 Feb. 26, 2004

(30) Foreign Application Priority Data

Aug. 12, 2002 (JP) ........................................ 2002-234890
Jan. 24, 2003 (JP) ........................................ 2003-016033
Jul. 24, 2003 (JP) ........................................ 2003-200941

(51) Int. Cl.[7] .......................... C07C 6/12; C07C 69/76; C07C 69/00; C07F 9/94
(52) U.S. Cl. .......................... 560/76; 560/96; 544/225; 546/2; 585/422
(58) Field of Search .................... 560/76, 96; 544/225; 546/2; 585/422

(56) References Cited

U.S. PATENT DOCUMENTS 4,581,469 A * 4/1986 Itatani et al. .................. 560/96

FOREIGN PATENT DOCUMENTS

| JP | 60-51150 | 3/1985 |
| JP | 61-106541 | 5/1986 |
| JP | 64-48 | 1/1989 |
| JP | 64-56649 | 3/1989 |
| JP | 2000-186063 | 7/2000 |

* cited by examiner

Primary Examiner—Cecilia J. Tsang
Assistant Examiner—Taylor V. Oh
(74) Attorney, Agent, or Firm—DLA Piper Rudnick Gray Cary US LLP

(57) ABSTRACT

A production process, especially a continuous production process, for a biphenyltetracarboxylic acid tetraester characterized by carrying out, in parallel, a step of preliminarily mixing a phthalic acid diester and a palladium compound-containing catalyst to prepare a starting mixture, a step of continuously or intermittently supplying the starting mixture to a reactor, a step of conducting oxidative dimerization reaction of the phthalic acid diester in a temperature range of from 140° C. and lower than 250° C. while supplying molecular oxygen to the reactor to form a reaction mixture in the reactor, and a step of continuously or intermittently removing a portion of the reaction mixture from the reactor. Preferably, the palladium compound-containing catalyst in the starting mixture is dissolved in the phthalic acid diester, the palladium compound-containing catalyst comprises a palladium compound, a bidentate ligand and a copper compound, the reactor consists of a plurality of serially connected reactors and a carboxylic acid is also continuously or intermittently supplied to the reactor.

13 Claims, 3 Drawing Sheets

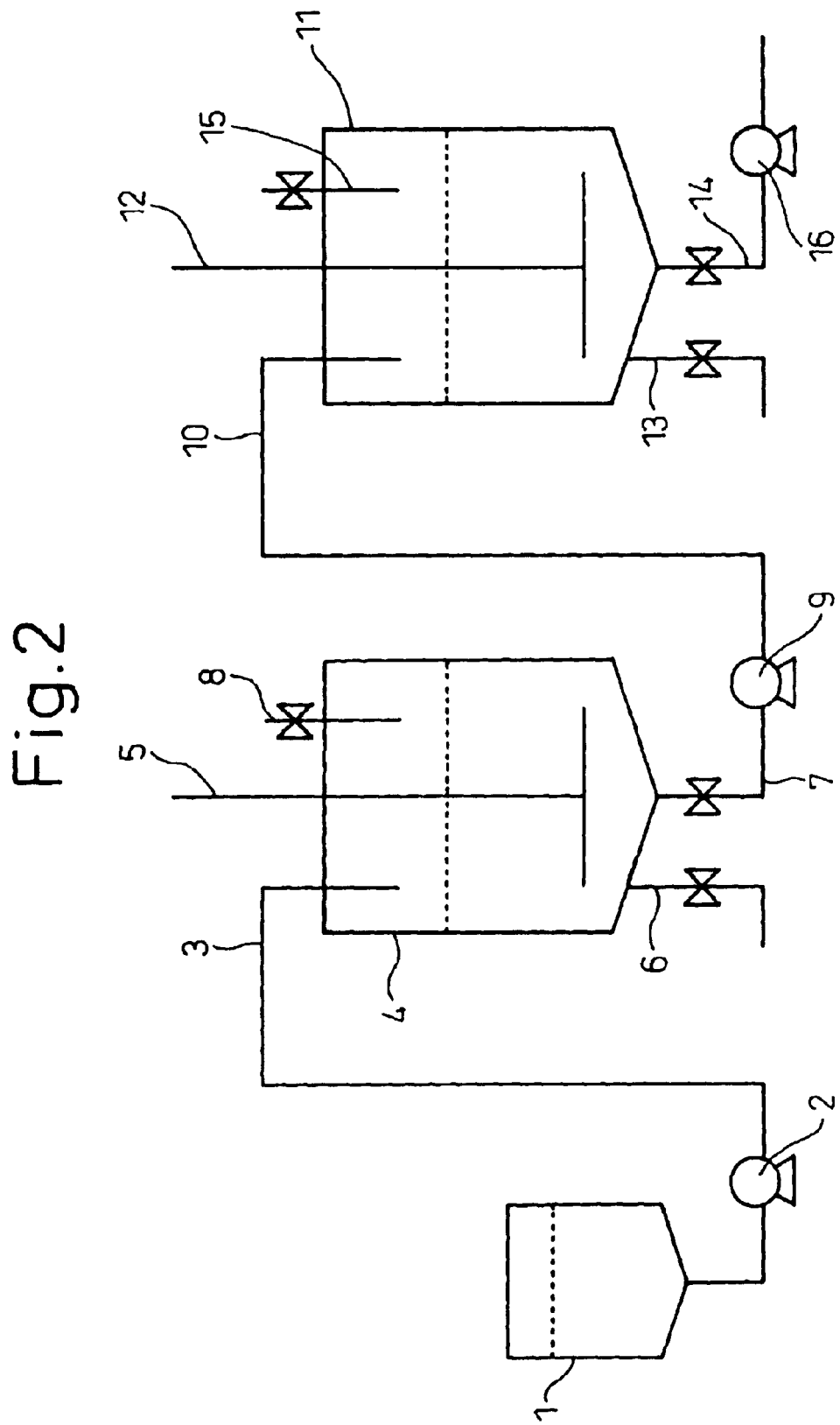

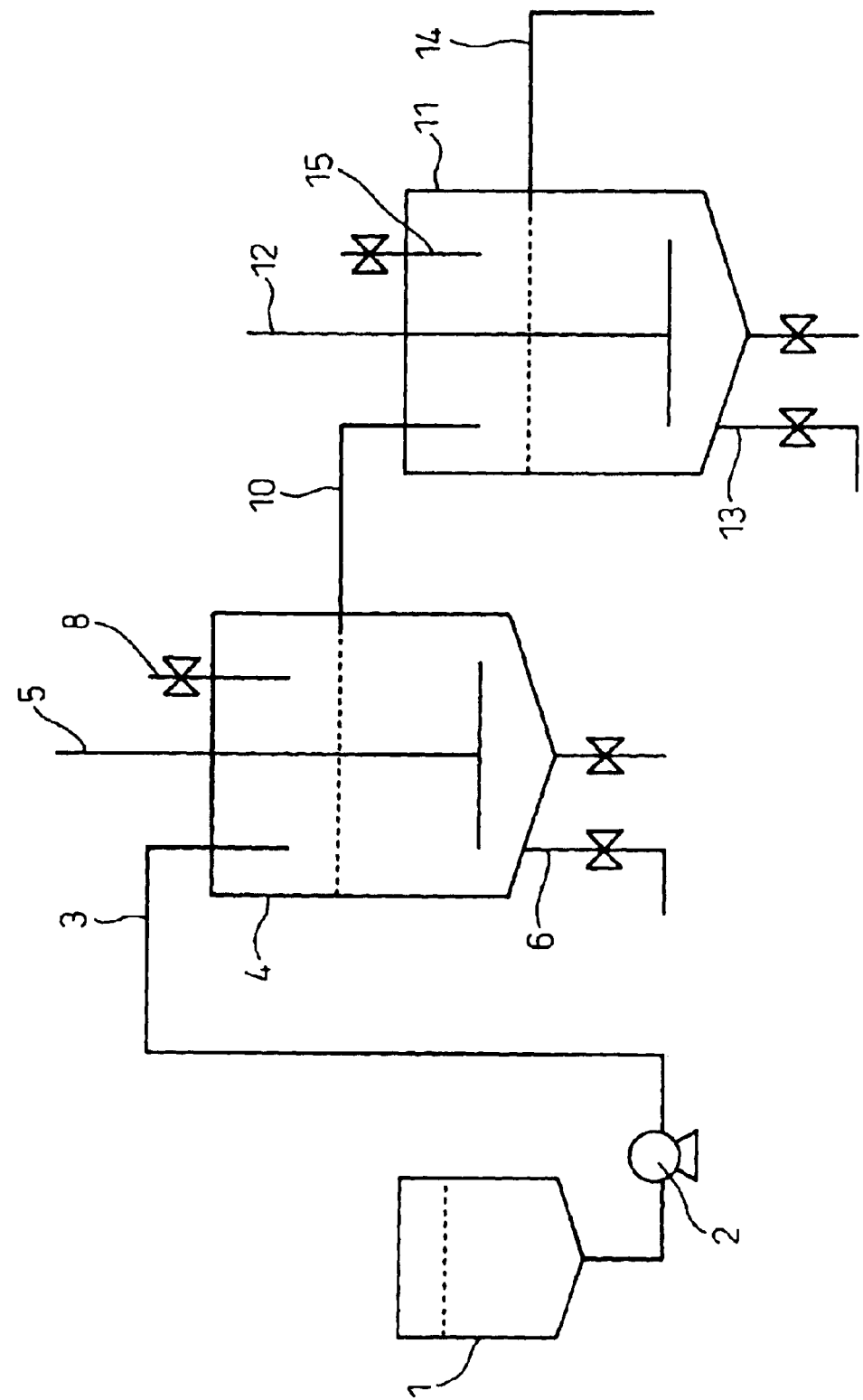

PROCESS FOR PRODUCTION OF BIPHENYLTETRACARBOXYLIC ACID TETRAESTERS

FIELD OF THE INVENTION

The present invention relates to an improved process for the production of biphenyltetracarboxylic acid tetraesters whereby a phthalic acid diester is subjected to an oxidative dimerization reaction in a molecular oxygen-containing atmosphere at high temperature and in the presence of a catalyst containing a palladium compound.

BACKGROUND OF THE INVENTION

Production of biphenyltetracarboxylic acid tetraesters, whereby a phthalic acid diester is subjected to oxidative dimerization reaction in a molecular oxygen-containing atmosphere at high temperature in the presence of a catalyst containing a palladium compound, is known. It is a drawback of this process, however, that the palladium compound-comprising catalyst is easily deactivated during the reaction, and various attempts have been made to overcome this drawback.

Japanese Unexamined Patent Publication SHO No. 60-51150 discloses a process for the production of biphenyltetracarboxylic acid esters wherein an ortho-phthalic acid ester is oxidatively coupled by supplying a molecular oxygen-containing gas to the reaction system at high temperature and in the presence of a catalyst comprising a palladium salt, a basic bidentate ligand and a copper salt, and is then further oxidatively coupled by successive addition of the catalyst component to the reaction system 1–10 times.

Japanese Unexamined Patent Publication SHO No. 61-106541 discloses a process for production of biphenyltetracarboxylic acid esters wherein a phthalic acid ester is oxidatively coupled while continuously or intermittently supplying a β-diketone to the reaction system at high temperature in a molecular oxygen-containing atmosphere in the presence of a catalyst comprising a palladium salt and a copper salt.

Japanese Unexamined Patent Publication SHO No. 64-48 discloses a process for production of biphenyltetracarboxylic acid tetraesters by oxidative dimerization of an ortho-phthalic acid diester in the presence of a catalyst comprising a palladium salt, a basic bidentate ligand and a copper salt, wherein the reaction mixture is circulated through the circulation line, and, the catalyst component is introduced through the circulation line of the reactor, to continuously replenish the catalyst component to the reactor.

Japanese Unexamined Patent Publication No. 2000-186063 discloses a process for production of 3,3',4,4'-biphenyltetracarboxylic acid tetraesters whereby an ortho-phthalic acid diester is dimerized by successive addition of a catalyst component comprising powdered palladium salt or compound with a specific surface area of 0.5 m$^2$/g or greater and a basic bidentate ligand compound.

All of these processes involve successive addition of the catalyst. Successive addition of the catalyst in these processes maintains catalytic activity for increased reaction efficiency. However, the processes are associated with several problems, including the requirement for special equipment, complicated procedures for successive catalyst addition, and difficulty in controlling the reaction because of rapid variation of the catalyst concentration(s) in the reaction mixture during addition of the catalyst(s), whereby improvement in reproductivity of a high reaction yield and a high selection of a target product is desired. Further, when the catalyst is successively supplied in large amounts during continuous prolonged reaction, greater production of by-products through reaction between the target product and the starting materials occurs, whereby reproductivity of a high reaction yield and a high selection of a target product for a long time period is desired.

In order to solve the problem of easy deactivation of catalysts comprising palladium compounds, additives which maintain the catalystic activity for longer periods have been investigated. Japanese Unexamined Patent Publication SHO No. 64-56649 discloses a process for production of biphenyltetracarboxylic acid esters wherein an ortho-phthalic acid diester is heated while supplying a molecular oxygen-containing gas to the reaction system in the presence of a catalyst comprising a divalent palladium salt, a copper salt and a basic bidentate ligand, wherein deactivation of the catalyst is limited by adding perchloric acid to the reaction system. However, the process cannot be considered practical because of the problem of risk of explosion involved in using perchloric acid.

Moreover, all of the production processes in the aforementioned patent publications are based on batch process. As the production processes therefore require a complicated procedure of heating or cooling at each start or termination of the reaction, they are also problematic in economical terms due to energy loss from heating and cooling and unavoidable material loss with opening of the apparatus for each loading during the batch operation, and the processes are therefore in need of improvement. However, none of the aforementioned patent publications have described concrete means or methods for improving continuous production process.

It is an object of the present invention to provide an improved economical process for production of biphenyltetracarboxylic acid tetraesters whereby a phthalic acid diester is subjected to an oxidative dimerization reaction at high temperature while supplying molecular oxygen to the reaction mixture in the presence of a catalyst containing a palladium compound, which process requires no special equipment or complicated procedures and allows effective utilization of the catalyst for easy control of the reaction and continuous production.

SUMMARY OF THE INVENTION

To attain the above object, the present invention provides the following:

(1) A production process, especially a continuous production process, for a biphenyltetracarboxylic acid tetraester, wherein the following steps are carried out in parallel:

a step of preliminarily mixing a phthalic acid diester and a palladium compound-containing catalyst to prepare a starting mixture, a step of continuously or intermittently supplying the starting mixture to a reactor, a step of conducting an oxidative dimerization reaction of the phthalic acid diester in a temperature range of from 140° C. to lower than 250° C. while supplying molecular oxygen to the reactor to form a reaction mixture in the reactor, and a step of continuously or intermittently removing a portion of the reaction mixture from the reactor.

(2) A production process for a biphenyltetracarboxylic acid tetraester according to (1) above wherein, in the starting mixture, the palladium compound-containing catalyst is dissolved in the phthalic acid diester.

(3) A production process for a biphenyltetracarboxylic acid tetraester according to (1) or (2) above, wherein the starting mixture is kept at a temperature in the range of 50–100° C. before being supplied to the reactor.

(4) A production process for a biphenyltetracarboxylic acid tetraester according to (1) to (3) above, wherein the palladium compound-containing catalyst comprises a palladium compound, a bidentate ligand and a copper compound.

(5) A production process for a biphenyltetracarboxylic acid tetraester according to (1) to (4) above, wherein the amount of the palladium compound is no more than 0.00093 mole with respect to one mole of the phthalic acid diester.

(6) A production process for a biphenyltetracarboxylic acid tetraester according to (4) or (5) above, wherein the copper compound is one selected from the group consisting of anhydrides or hydrates of copper propionate, copper n-butyrate, copper bis(acetylacetonate) and copper pivalate.

(7) A production process for a biphenyltetracarboxylic acid tetraester according to (1) to (6) above, wherein a carboxylic acid is also continuously or intermittently supplied to the reactor.

(8) A production process for a biphenyltetracarboxylic acid tetraester according to (7) above, wherein the carboxylic acid is one selected from the group consisting of acetic acid, trifluoroacetic acid, propionic acid, pivalic acid and butyric acid.

(9) A production process for a biphenyltetracarboxylic acid tetraester according to (1) to (8) above, wherein the reactor comprises a plurality of serially connected reactors, the process comprising a step of continuously or intermittently supplying the starting mixture to a first reactor, a step of continuously or intermittently removing a portion of the reaction mixture from each reactor and successively introducing it into the next reactor, a step of conducting oxidative dimerization of the phthalic acid diester in a temperature range of from 140° C. and lower than 250° C. while supplying molecular oxygen to each reactor to form a reaction mixture and a step of continuously or intermittently removing a portion of the reaction mixture from the final reactor, wherein the steps are carried out in parallel.

(10) A production process for a biphenyltetracarboxylic acid tetraester employing a plurality of serially connected reactors including at least a first reactor and a second reactor, the process comprising a step of preliminarily mixing a phthalic acid diester and a palladium compound-containing catalyst to prepare a starting mixture, a step of continuously or intermittently supplying the starting mixture to the first reactor, a step of conducting oxidative dimerization reaction of the phthalic acid diester in a temperature range of from 140° C. and lower than 250° C. while supplying molecular oxygen to the first reactor to form a reaction mixture in the first reactor, a step of continuously or intermittently removing a portion of the reaction mixture from the first reactor and introducing it into the second reactor, a step of conducting oxidative dimerization of the phthalic acid diester in a temperature range of from 140° C. and lower than 250° C. while supplying molecular oxygen to the second reactor to form a reaction mixture in the second reactor, a step of continuously or intermittently removing a portion of the reaction mixture from the second reactor, and a step of repeating the same procedure as above for each reactor after the second reactor if present, wherein the steps are carried out in parallel.

(11) A production process for a biphenyltetracarboxylic acid tetraester according to (10) above, wherein a carboxylic acid is also continuously or intermittently supplied to each of the reactors.

(12) A production process for a biphenyltetracarboxylic acid tetraester, comprising producing a biphenyltetracarboxylic acid tetraester by an oxidative dimerization reaction of a phthalic acid diester at high temperature while supplying molecular oxygen in the presence of a catalyst comprising a palladium compound, a bidentate ligand and a copper compound, wherein a carboxylic acid is further supplied continuously or intermittently.

(13) A production process for a biphenyltetracarboxylic acid tetraester according to (12), wherein the boiling point of the carboxylic acid is below the oxidative dimerization reaction temperature.

(14) A production process for a biphenyltetracarboxylic acid tetraester according to (12) or (13) above, wherein the carboxylic acid is one selected from the group consisting of acetic acid, trifluoroacetic acid, propionic acid, pivalic acid and butyric acid.

BRIEF DESCRIPTION OF THE DRAWINGS

FIG. 2 is a schematic illustration of another embodiment of a reactor used for the production process of the invention.

FIG. 3 is a schematic illustration of another embodiment of a reactor used for the production process of the invention.

MODES OF CARRYING OUT THE INVENTION

Figure 1:
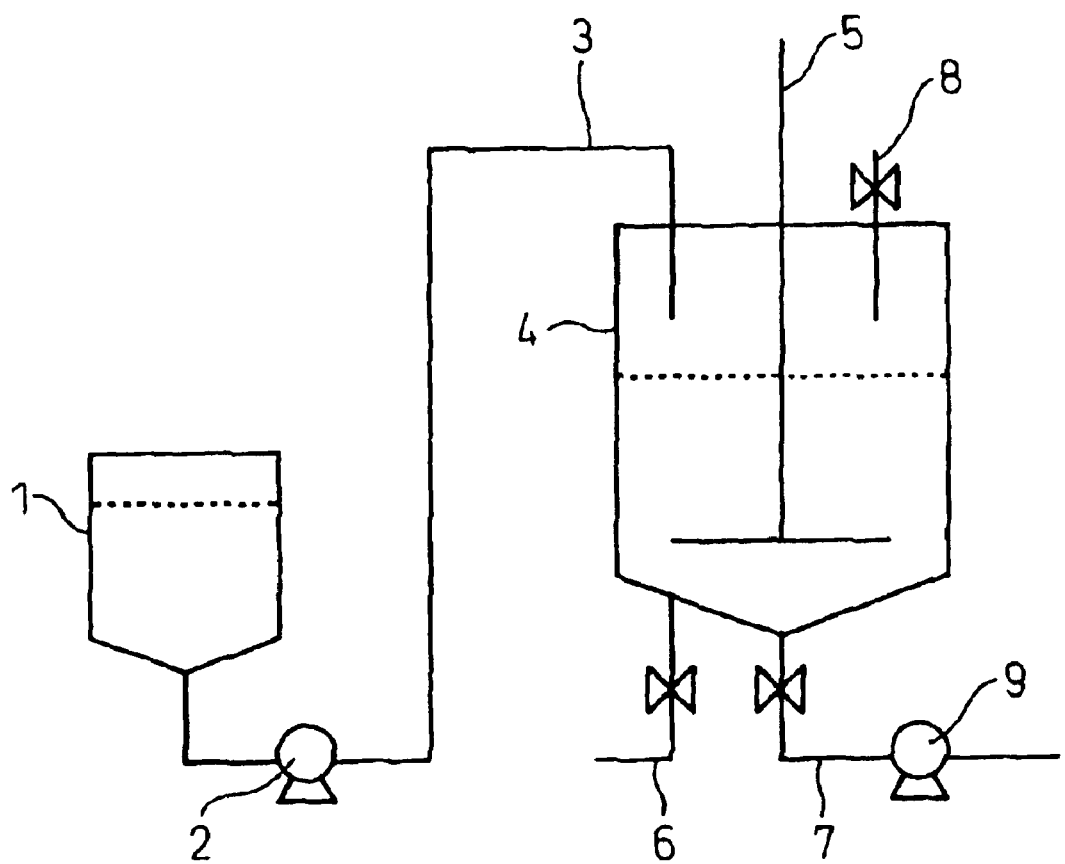
FIG. 1 is a schematic illustration of an embodiment of a reactor used for the production process of the invention.

The process for production of biphenyltetracarboxylic acid tetraesters according to the invention is a continuous production process characterized by carrying out in parallel a step of continuously or intermittently supplying a preliminarily mixed mixture of a phthalic acid diester and a palladium compound-containing catalyst to a reactor, a step of conducting oxidative dimerization reaction of the phthalic acid diester in a temperature range of from 140° C. and lower than 250° C. while supplying molecular oxygen to the reactor, and a step of continuously or intermittently removing a portion of the reaction mixture from the reactor. The active palladium compound-containing catalyst is maintained homogeneously and in the desired concentration in the reaction mixture during the continuous production process. In a preferred mode of the invention, all the above steps are carried out simultaneously in parallel.

Specifically, the phthalic acid diester starting material and the palladium compound-containing catalyst are first supplied to the reactor in the prescribed amounts. This is followed by oxidative dimerization of the phthalic acid diester while maintaining the prescribed constant amount of reaction mixture in the reactor during the continuous reaction by approximately equally adjusting (1) the supply of the phthalic acid diester starting material and the palladium compound-containing catalyst to the reactor and (2) the removal of the reaction mixture from the reactor. As the preferred prescribed amounts and concentrations of the phthalic acid diester starting material and catalyst are thus maintained in the reactor, it is possible to consistently accomplish oxidative dimerization of the phthalic acid diester in a satisfactory manner.

The step of supplying the phthalic acid diester and palladium compound-containing catalyst to the reactor and the step of removing the reaction mixture from the reactor are carried out in parallel while keeping a balance between supply and removal, and the supply and removal steps may be conducted continuously or intermittently so long as the oxidative dimerization can be accomplished in a continuous manner while maintaining the prescribed amount of the reaction mixture in the reactor.

However, in the present invention, as the step of supplying the phthalic acid diester starting material and the palladium compound-containing catalyst to the reactor and the step of removing the reaction mixture from the reactor do not require complicated procedures or complex equipment and can be carried out easily using a simple liquid conveying pump, they are preferably carried out in a continuous fashion.

According to the invention, the phthalic acid diester starting material and palladium compound-containing catalyst are supplied to the reactor as a homogeneously mixed or stirred mixture, and preferably as a homogeneously dissolved mixture, in a prescribed compositional ratio suitable for oxidative dimerization of the phthalic acid diester and the palladium compound-containing catalyst. By supplying the phthalic acid diester and the palladium compound-containing catalyst as an already homogeneously mixed mixture to the reactor, it is possible to constantly maintain the concentration of the active palladium compound-containing catalyst in the reaction mixture to the preferred concentration for long periods.

Supplying the phthalic acid diester starting material and the palladium compound-containing catalyst separately not only introduces an inconvenience in requiring separate supply equipment, but also results in non-homogeneous concentrations of the starting material and catalyst in the reaction mixture. This complicates control of the reaction and tends to lead to problems such as lower production of the target compound and increased production of by-products and results in low repeatability of a desired reaction yield and selectivity of the target product. Even when the phthalic acid diester starting material and the palladium compound-containing catalyst are supplied together, if they are not supplied as a homogeneously mixed or stirred mixture, and preferably as a homogeneously dissolved mixture, concentrations of the starting material and catalyst in the reaction mixture become non-homogeneous resulting in complicating control of the reaction, tending to lead to problems such as lower production of the target compound and increased production of by-products and thus resulting in low reproductivity of a desired reaction yield and selectivity of the target product.

The phthalic acid diester starting material and palladium compound-containing catalyst are most preferably supplied to the reactor as a homogeneously dissolved mixture. Without dissolution of the palladium compound-containing catalyst in the phthalic acid diester, an inconvenience may possibly arise where it is necessary to continue stirring with a large stirrer or to use the catalyst supply apparatus in order to consistently maintain a homogeneously mixed state of the palladium compound-containing catalyst in the phthalic acid diester.

If the palladium compound-containing catalyst is first homogeneously dissolved in the phthalic acid diester starting material in the prescribed concentration preferred for oxidative dimerization to prepare a mixed solution, and this mixed solution is supplied, then it will be easier to keep the concentration of the active palladium compound-containing catalyst at the preferred concentration with respect to the phthalic acid diester in the reaction mixture, and thus much easier to achieve uniform proceeding of the reaction and better control of the reaction.

The phthalic acid diester starting material and palladium compound-containing catalyst are preferably heated to dissolution at a temperature of 50–100° C. and the mixed solution kept in a temperature range of 50–100° C. until being supplied to the reactor. Such heating will aid homogeneous dissolution of the catalyst and limit fluctuation in the catalyst concentration and in the temperature of the reaction mixture when it is supplied to the reactor, to facilitate control of the reaction. The mixed solution is preferably not kept at a temperature above 100° C., as the phthalic acid diester and palladium compound-containing catalyst will undergo stoichiometric oxidative dimerization although at a slow reaction rate, and the reoxidation rate will be exceedingly low due to a lack of molecular oxygen, resulting in deposition of the palladium and making it impossible to achieve a fixed supply (concentration) of the catalyst.

According to the invention, the preferred compositional ratio of the phthalic acid diester and palladium compound-containing catalyst is usually at least 0.00001 mole and especially at least 0.00005 mole and no greater than 0.01 mole and especially no greater than 0.001 mole, of the palladium compound with respect to one mole of the phthalic acid diester, but according to the invention the palladium compound is used at more preferably no greater than 0.00093 mole with respect to one mole of the phthalic acid diester to facilitate dissolution of the palladium compound-containing catalyst during the oxidative dimerization.

According to the invention, the oxidative dimerization of the phthalic acid diester is carried out in a temperature range of 140° C. or higher and preferably 200° C. or higher, and lower than 250° C. and preferably no higher than 240° C.

If the reaction temperature for the oxidative dimerization of the phthalic acid diester is 250° C. or higher, not only the palladium compound-containing catalyst becomes deactivated as the oxidative dimerization proceeds, but also the catalyst itself becomes deactivated by thermal decomposition, thereby complicating control of the reaction and notably reducing the yield of the oxidative reaction product. On the other hand, a temperature below 140° C. is not preferred because the oxidative dimerization reaction rate will be insufficient.

In a reaction for oxidative dimerization of a phthalic acid diester at high temperature while supplying molecular oxygen in the presence of a palladium compound-containing catalyst, when the catalyst is added successively, according to prior art processes, the amount of catalyst to add and the timing of addition cannot be determined in response to actual reduction in the catalytic activity because it is difficult to directly detect how much of the active catalyst actually remains in the reaction mixture. In other words, it is difficult in practice to control the reaction by successive addition of the catalyst.

According to the present invention, however, the phthalic acid diester starting material and the palladium compound-containing catalyst are continuously supplied in the prescribed compositional ratio to promote oxidative dimerization. As a result, if the reaction temperature for oxidative dimerization is in the range of least 140° C. and lower than 250° C., the oxidative dimerization can be easily controlled because the active catalyst concentration in the reactor can be kept at the preferred fixed concentration. In other words, the oxidative dimerization can be suitably controlled continuously for a long period without any special apparatuses or complicated procedures for successive addition of the catalyst.

According to the invention, the reactor may consist of a series of connected reactors, and is most preferably composed of 2 to 6 reactors. A single reactor is not advantageous from the standpoint of effective use of the catalyst, since it is difficult to avoid removing part of the catalyst which still exhibits sufficiently high activity from the reactor immediately after its supply.

By constructing the reactor (reaction apparatus) as a series of connected reactors, continuously or intermittently supplying the phthalic acid diester starting material and the palladium compound-containing catalyst to the first reactor, continuously or intermittently removing the reaction mixture from each reactor and introducing it, in order, to the next reactor while supplying molecular oxygen to each reactor for oxidative dimerization of the phthalic acid diester, and continuously or intermittently removing the reaction mixture from the final reactor, it is possible to effectively avoid removing the catalyst which still exhibits sufficiently high activity from the reactor immediately after its supply, thereby facilitating effective use of the catalyst.

When the reactor is constructed as a series of connected reactors, the amounts of the reaction mixture in each reactor of the reactor during the continuous reaction are kept at the respective prescribed amounts. Specifically, after the reaction mixture in each reactor has reached the prescribed amount, the supply amount of the phthalic acid diester starting material and palladium compound-containing catalyst in the first reactor, the amount of the reaction mixture introduced in order from each reactor to each subsequent reactor and the amount of reaction mixture removed from the final reactor are all adjusted to be roughly equivalent.

As a result, the phthalic acid diester starting material, the catalyst and the reaction product in each of the reactors are kept at the preferred prescribed amounts and prescribed concentrations to allow optimum oxidative dimerization of the phthalic acid diester.

According to the invention, the reaction temperature for the oxidative dimerization when the reactor is constructed as a series of connected reactors may be the same or different for each reactor. Particularly, the reaction temperature for each reactor is in the range of from 140° C. and lower than 250° C., and the reaction temperature for the (n+1)th reactor is preferably higher than the reaction temperature for the nth reactor (where n is an integer of 1 or greater).

The phthalic acid diester used for the invention is represented by the following chemical formula (1).

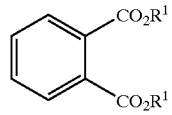

(1)

wherein each $R^1$ independently represents alkyl or aryl, which may be optionally substituted.

As preferred phthalic acid diesters to be used for the invention there may be mentioned, specifically, dimethyl phthalate, diethyl phthalate, dipropyl phthalate, dibutyl phthalate, dioctyl phthalate and diphenyl phthalate.

The phthalic acid diester may be easily obtained by reaction of phthalic acid, phthalic anhydride or a phthalic acid halide with a compound having a terminal hydroxyl group, such as a lower aliphatic alcohol or aromatic alcohol.

The palladium compound-containing catalyst used for the invention may be a palladium compound catalyst, a catalyst comprising a combination of a palladium compound and a ligand, a catalyst comprising a combination of a palladium compound and a copper compound, or a catalyst comprising a combination of a palladium compound, a ligand and a copper compound.

A catalyst comprising a combination of a palladium compound, a bidentate ligand and a copper compound is particularly preferred for a high oxidative dimerization reaction product yield and selective production of specific isomers.

As palladium compounds to be used for the invention there may be mentioned palladium chloride, palladium bromide, palladium iodide, palladium nitrate, palladium sulfate, palladium acetate, palladium trifluoroacetate, palladium propionate, palladium pivalate, palladium trifluoromethanesulfonate, palladium bis(acetylacetonate) and palladium bis(1,1,1,5,5,5-hexafluoroacetylacetonate), with palladium acetate, palladium propionate, palladium pivalate, palladium trifluoroacetate and palladium nitrate being preferred because of their high catalytic activity.

According to the invention, the preferred compositional ratio of the phthalic acid diester and palladium compound-containing catalyst is at least 0.00001 mole and especially at least 0.00005 mole and no greater than 0.01 mole and especially no greater than 0.001 mole, of the palladium compound with respect to one mole of the phthalic acid diester, but according to the invention the palladium compound is more preferably no greater than 0.00093 mole with respect to one mole of the phthalic acid diester to facilitate dissolution of the palladium compound-containing catalyst in the phthalic acid diester during the oxidative dimerization. The amount of the palladium compound is preferably not less than 0.00001 mole with respect to one mole of the phthalic acid diester starting material because, although the reaction will proceed, the reaction rate will be slowed. Although the palladium compound may be used in an amount exceeding 0.01 mole with respect to one mole of the phthalic acid diester starting material, this is not economical in terms of the catalyst cost.

The ligand used for the invention is preferably a bidentate ligand capable of bidentate coordination with palladium, and especially preferred are bidentate ligands which can form complexes with palladium through two nitrogen atoms, bidentate ligands which can form complexes with palladium through two oxygen atoms, and bidentate ligands which can form complexes with palladium through a nitrogen and an oxygen atom.

As examples of bidentate ligands which can form complexes with a palladium salt or compound through two nitrogen atoms, there are preferably used bidentate ligands represented by chemical formulas (2) and (3) below.

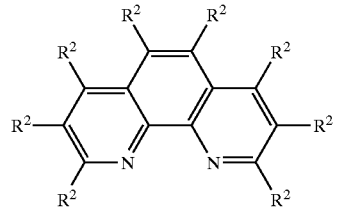

(2)

wherein each $R^2$ independently represents hydrogen, halogen, hydroxyl, nitro, amino, alkyl, alkoxy or aryl, where alkyl, alkoxy and aryl may be optionally substituted.

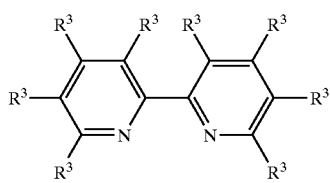

(3)

wherein each R³ independently represents hydrogen, halogen, hydroxyl, nitro, amino, alkyl, alkoxy or aryl, where alkyl, alkoxy and aryl may be optionally substituted.

By using these ligands it is possible to selectively obtain symmetric biphenyltetracarboxylic acid tetraesters. Specifically, it is possible to selectively produce 3,3',4,4'-biphenyltetracarboxylic acid tetraesters as symmetrically dimerized products while suppressing production of 2,3,3',4'-biphenyltetracarboxylic acid tetraesters as asymmetrically dimerized products.

As specific preferred examples of bidentate ligands represented by chemical formulas (2) and (3) there may be mentioned 1,10-phenanthroline and 2,2'-bipyridyl. Especially preferred is 1,10-phenanthroline because of its strong effect of promoting oxidative dimerization and because its complex in coordination with palladium is highly soluble in phthalic acid diesters.

As preferred examples of bidentate ligands which can form complexes with a palladium salt or compound through two oxygen atoms, there may be mentioned β-diketones such as acetylacetone, benzoylacetone, 1,3-diphenyl-1,3-propanedione, 1,1,1-trifluoroacetylacetone, 2,4-hexanedione, 2,4-pentanedione, 1,1,1-trifluoro-2,4-hexanedione and 1,1,1,5,5,5-hexafluoroacetylacetone.

As preferred examples of bidentate ligands which can form complexes with a palladium salt or compound through a nitrogen and an oxygen atom, there may be mentioned nitrogen-containing heterocyclic compounds with oxygen on a substituent, such as pyridinecarboxylic acid, pyridinecarboxylic acid methyl ester, pyridinecarboxylic acid ethyl ester, pyrazinecarboxylic acid, pyrazinecarboxylic acid methyl ester, pyrazinecarboxylic acid ethyl ester, quinolinecarboxylic acid, isoquinolinecarboxylic acid, hydroxyquinoline, 2-benzoylpyridine and 2-pyridylamide, or aliphatic amines with oxygen on a substituent, such as N,N-dimethylglycine or N,N-dimethylacetamide.

By using the aforementioned bidentate ligands which can form complexes with a palladium salt or compound through two oxygen atoms or bidentate ligands which can form complexes with a palladium salt or compound through a nitrogen and an oxygen atom, it is possible to selectively obtain asymmetrically dimerized products. Specifically, it is possible to selectively produce the asymmetrically dimerized products 2,3,3',4'-biphenyltetracarboxylic acid tetraesters while suppressing production of the symmetrically dimerized products 3,3',4,4'-biphenyltetracarboxylic acid tetraesters.

These bidentate ligands are preferably added at 0.1–5 moles with respect to one mole of the palladium compound, and more preferably at 0.5–1.5 moles with respect to one mole of the palladium compound. At less than 0.1 mole with respect to one mole of the palladium compound, satisfactory selectivity cannot be achieved. At greater than 5 moles with respect to one mole of the palladium compound, the catalytic activity may be reduced.

According to the invention, a palladium compound may be used together with a copper compound as the catalyst to limit deactivation of the catalyst even with a low oxygen partial pressure during the reaction. Since oxidative dimerization is therefore possible at atmospheric pressure or near atmospheric pressure by using a palladium compound together with a copper compound, this is particularly preferred for continuous production according to the invention.

As copper compounds to be used for the invention there may be preferably mentioned copper acetate, copper propionate, copper n-butyrate, copper 2-methylpropionate, copper pivalate, copper lactate, copper butyrate, copper benzoate, copper trifluoroacetate, copper bis(acetylacetonate), copper bis(1,1,1,5,5,5-hexafluoroacetylacetonate), copper chloride, copper bromide, copper iodide, copper nitrate, copper nitrite, copper sulfate, copper phosphate, copper oxide, copper hydroxide, copper trifluoromethanesulfonate, copper para-toluenesulfonate and copper cyanide. Particularly preferred for a strong effect of promoting oxidative dimerization are copper acetate, copper propionate, copper n-butyrate, copper pivalate and copper bis(acetylacetonate), among which copper propionate, copper n-butyrate, copper pivalate and copper bis(acetylacetonate) are most preferred for the production process of the invention because they dissolve readily in phthalic acid diester starting materials.

These copper compounds may also be used as anhydrides or hydrates.

The amount of the copper compound to be added according to the invention is preferably 0.01–10 moles and especially 0.1–2.0 moles with respect to one mole of the palladium compound. If the amount of the copper compound is less than 0.01 mole with respect to one mole of the palladium compound, the oxygen partial pressure cannot be lowered during the reaction, while an amount exceeding 10 moles with respect to one mole of the palladium compound is not economical.

The present invention may be carried out with or without a reaction solvent. Industrially, the reaction is more preferably conducted in the substantial absence of a solvent. When a reaction solvent is used, there may be mentioned as examples organic acid esters such as ethyleneglycol diacetate and dimethyl adipate, or ketones such as n-butylmethyl ketone, methylethyl ketone and isopropylethyl ketone. It may be used, for example, at no greater than a 10,000-fold volume and preferably no greater than a 1000-fold volume with respect to the starting phthalic acid diester.

According to the invention, the molecular oxygen may be supplied as pure oxygen gas, but considering the risk of explosion, it is preferred to use air or an oxygen-containing mixed gas diluted with an inert gas such as nitrogen or carbon dioxide gas to an oxygen content of approximately 5 vol % to 50 vol %. The oxygen-containing mixed gas or air is preferably supplied at a rate of about 1–20,000 ml/min and especially 10–10,000 ml/min to 1000 ml of the reaction mixture, with bubbling to evenly diffuse it through the reaction mixture, and preferably with bubbling using a filter.

According to the invention, the oxidative dimerization may be carried out at ordinary pressure or under pressure up to 200 atmospheres and preferably no greater than 50 atmospheres, but the reaction is most preferably conducted at atomospheric pressure to simplify the equipment and procedure. The oxidative dimerization of the invention is preferably carried out with an oxygen partial pressure of 0.01–200 atmospheres and preferably 0.05–50 atmospheres.

According to the invention, a carboxylic acid is preferably supplied continuously or intermittently during production of the biphenyltetracarboxylic acid tetraester by oxidative dimerization reaction of the phthalic acid diester at high temperature while supplying molecular oxygen in the presence of a catalyst comprising a palladium compound, a bidentate ligand and a copper compound.

This is another mode of the invention which facilitates prolonged stable oxidative dimerization of the phthalic acid diester by the palladium compound-containing catalyst.

According to the invention which is characterized by carrying out in parallel a step of continuously or intermittently supplying a preferably homogeneous mixture of a phthalic acid diester and a palladium compound-containing catalyst, a step of conducting oxidative dimerization of the phthalic acid diester in a temperature range of from 140° C. and lower than 250° C. while supplying molecular oxygen in the reactor, and a step of continuously or intermittently removing out a portion of the reaction mixture from the reactor, it is highly preferred for a carboxylic acid to be continuously or intermittently supplied to the reactor for stable oxidative dimerization in a continuous manner for longer periods.

In other words, according to the invention, a carboxylic acid is supplied to the reaction mixture as an additive to maintain the catalytic activity for a longer period. Since the presence of a carboxylic acid in the reaction mixture can suppress deactivation of the palladium compound-containing catalyst, it allows the palladium compound-containing catalyst to be used more effectively, or stated differently, it allows improvement in the catalyst turnover number while maintaining a consistent level of activity of the palladium compound-containing catalyst for a longer period, thereby facilitating stable control of the oxidative dimerization for prolonged periods and limiting production of by-products.

According to the invention, continuously or intermittently supplying a carboxylic acid to constantly maintain the presence of the carboxylic acid in the reaction mixture is particularly effective for stabilizing the catalystic activity and improving the catalytic turnover number. The carboxylic acid may be supplied alone, or it may be combined with the mixture of the phthalic acid diester and palladium compound-containing catalyst, or supplied in association with the molecular oxygen. A liquid carboxylic acid may be supplied with a simple liquid conveying pump, which requires no complex procedures or complicated equipment. It is therefore preferably supplied continuously to the reaction system with a liquid conveying pump. Also, the vapor pressure of the carboxylic acid is preferably controlled by heating or the like so that the carboxylic acid vapor associates with the molecular oxygen for continuous supply to the reaction system. The carboxylic acid used for the invention may be a monocarboxylic acid, or a polycarboxylic acid having two or more carboxyl groups in the molecule, but monocarboxylic acids such as acetic acid, trifluoroacetic acid, propionic acid, butyric acid and pivalic acid are preferred for a higher effect of stabilization of the catalystic activity and improvement of the catalyst turnover number. A carboxylic anhydride may also be used instead of the carboxylic acid, because a carboxylic anhydride readily converts to the corresponding carboxylic acid in the reaction system due to generally rapid hydrolysis of the carboxylic anhydride by water produced from the oxidative dimerization.

According to the invention, the carboxylic acid is preferably not present in a large amount in the reaction system because this may reduce the catalystic activity and thereby inhibit the oxidative dimerization. As a large amount of the carboxylic acid in the reaction system will promote hydrolysis of the ester group by the water produced by the oxidative dimerization, due to the reaction catalyzed by the carboxylic acid, the phthalic acid diester will be readily converted to phthalic acid. Aromatic compounds with carboxyl groups such as phthalic acid have lower reactivity in oxidative dimerization than aromatic compounds with ester groups, and therefore the oxidative dimerization will be inhibited.

It is therefore undesirable for the carboxylic acid to be present in a large amount in the reaction system for a prolonged period, and thus the excess carboxylic acid is preferably ejected periodically or continuously out of the reaction system. A carboxylic acid with a boiling point below the reaction temperature is especially preferred for easier ejection of the excess carboxylic acid out of the reaction system, as carboxylic acid vapor, during the reaction. As carboxylic acids with boiling points below ordinary reaction temperatures for oxidative dimerization there may be preferably mentioned acetic acid (boiling point: 118° C.) and trifluoroacetic acid (boiling point: 72° C.).

Also, as mentioned above, the carboxylic acid is most effectively supplied to the reaction system either continuously or intermittently in order to stabilize the catalytic activity and improve the catalytic turnover number, and therefore according to the invention, the oxidative dimerization is preferably carried out while supplying the carboxylic acid continuously or intermittently to the reaction system and simultaneously ejecting the carboxylic acid in the reaction system out of the reaction system as carboxylic acid vapor, either continuously or intermittently.

In consideration of the risk of explosion of the carboxylic acid and oxygen when the carboxylic acid is supplied to the reaction system while controlling the carboxylic acid vapor and associating the carboxylic acid vapor with the molecular oxygen, it is preferred to use an oxygen-containing gas mixture diluted with an inert gas such as nitrogen or carbon dioxide gas, or air, as the molecular oxygen-containing gas. The amount of carboxylic acid supplied to the reaction system is preferably at least 0.01 mole and less than 50 moles per hour, and especially 0.1–30 moles per hour, with respect to one mole of the palladium compound used. With a carboxylic acid supply amount of less than 0.01 mole, the effect of addition is minimal, while an amount of 50 moles or greater is economically disadvantageous and can result in inhibition of the oxidative dimerization due to retention of the excess carboxylic acid in the reaction system.

There are no particular restrictions on the reactor used for the invention, and there may be used a single-tank or multitank complete mixing reactor, with a single reactor or multiple reactors, a multitubular heat exchanger type tubular reactor, or a tower reactor. The material of the reactor is also not particularly restricted, but preferably a glass or SUS reactor, for example, is used.

The process for production of biphenyltetracarboxylic acid tetraesters of the invention will now be explained in greater detail through schematic illustrations showing embodiments of reactors in FIG. 1, FIG. 2 and FIG. 3. However, the invention is not limited to these embodiments.

In FIG. 1, a phthalic acid diester starting material and a catalyst are combined in a prescribed proportion in a starting material tank 1, where the dissolved starting mixture is kept at a prescribed temperature. The starting mixture is then introduced from a starting material supply conduit 3 into a reactor 4 at a prescribed rate by a liquid conveying pump 2. The reactor 4 is provided with a heater (not shown), a stirrer 5, an air supply conduit 6, a reaction mixture removal conduit 7 and a gas extraction conduit 8. The starting mixture comprising the phthalic acid diester and catalyst, etc. which is introduced into the reactor is oxidatively dimerized with bubbling a prescribed amount of air into the reaction mixture from the air supply conduit 6 at a prescribed temperature while stirring. The gas extraction conduit 8 is open to the atmosphere via a collector (not shown) for the low boiling substances and vaporized phthalic acid diester with a cooling condenser, and the gas in the reactor is ejected out of the reactor through the gas extraction conduit 8 by the air introduced by bubbling. The reaction mixture is removed from the reaction mixture removal conduit 7 via a liquid conveying pump 9, in an amount roughly equivalent to the amount of starting mixture supplied to the reactor 4. The reaction mixture in the reactor is kept at the prescribed temperature during the reaction, and the amount is kept approximately constant by maintaining approximately equivalent amounts of the supplied starting mixture and the removed reaction mixture.

In FIG. 2, the reactor comprises two serially connected reactors 4 and 11. The reactor 4 is provided with a heater (not shown), a stirrer 5, an air supply conduit 6, a reaction mixture removal conduit 7 and a gas extraction conduit 8. The reactor 11 is also provided with a heater (not shown), a stirrer 12, an air supply conduit 13, a reaction mixture removal conduit 14 and a gas extraction conduit 15.

In the starting material tank 1, the mixed and dissolved starting mixture comprising the phthalic acid diester starting material, catalyst, etc. in the prescribed proportions is kept at a prescribed temperature. The starting mixture is introduced into the reactor 4 at a prescribed rate from the starting material supply conduit 3 by a liquid conveying pump 2. The starting mixture introduced into the reactor 4 is oxidatively dimerized with bubbling a prescribed amount of air into the reaction mixture from the air supply conduit 6 at a prescribed temperature while stirring. The gas extraction conduit 8 is open to the atmosphere via a collector (not shown) for the low boiling substances and vaporized phthalic acid diester with a cooling condenser, and the gas in the reactor is ejected out of the reactor through the gas extraction conduit 8 by the air introduced by bubbling. The reaction mixture is removed from the reaction mixture removal conduit 7 via a liquid conveying pump 9, in an amount roughly equivalent to the amount of starting mixture supplied to the reactor 4, and the reaction mixture is supplied to the reactor 11 from a reaction mixture supply conduit 10. The reaction mixture in the reactor 4 is kept at the prescribed temperature during the reaction, and the amount is kept approximately constant by maintaining approximately equivalent amounts of the supplied starting mixture and the removed reaction mixture.

The reaction mixture introduced into the reactor 11 is further oxidatively dimerized with bubbling a prescribed amount of air into the reaction mixture from the air supply conduit 13 at a prescribed temperature while stirring. The gas extraction conduit 15 is open to the atmosphere via a collector (not shown) for the low boiling substances and vaporized phthalic acid diester with a cooling condenser, and the gas in the reactor is ejected out of the reactor through the gas extraction conduit 15 by the air introduced by bubbling. The reaction mixture in the reactor 11 is removed from the reaction mixture removal conduit 14 via a liquid conveying pump 16, in an amount roughly equivalent to the amount of starting mixture supplied. The reaction mixture in the reactor 11 is kept at the prescribed temperature during the reaction, and the amount is kept approximately constant by maintaining approximately equivalent amounts of the supplied starting mixture and the removed reaction mixture.

FIG. 3 shows a production apparatus comprising two reactors 4, 11 serially connected in the same manner as FIG. 2, which are used for the same process as shown in FIG. 2, but without a liquid conveying pump for removal of the reaction mixture from the reactor 4 and introduction into the reactor 11. The reaction mixture removal conduit is situated at a prescribed height on the reactor 4 and the reactor 11 is placed at a lower position so that the removed reaction mixture flows downward by its own weight, such that the overflow portion is introduced by its own weight into the reactor 11 from the reactor 4. In addition, removal of the reaction mixture from the reactor 11 is also accomplished by overflow. This arrangement is preferred because it facilitates introduction of the reaction mixture from one reactor to the next in an amount equal to the amount supplied, thereby allowing the prescribed amount of reaction mixture to be easily maintained in each reactor.

According to the continuous production process of the invention, the reaction mixture removed from the final reactor is stored in a tank if necessary. The target biphenyltetracarboxylic acid tetraester compound may be obtained by separation and purification from the reaction mixture by a post-processing step utilizing well-known means such as a distillation or crystallization procedure.

The biphenyltetracarboxylic acid tetraester obtained by the continuous production process of the invention is very important as a starting material for polyimide resins, for example.

The biphenyltetracarboxylic acid tetraester may be hydrolyzed to biphenyltetracarboxylic acid by a method of hydrolysis at high temperature and high pressure, or a method of hydrolysis by addition of an acid or alkali. Heating at high temperature for anhydration can yield biphenyltetracarboxylic dianhydride. The dianhydride is useful as a monomer starting material for polyimide production, or as an epoxy resin curing agent or the like.

The present invention as described above exhibits the following effects.

The process of the invention for producing a biphenyltetracarboxylic acid tetraester by oxidative dimerization of a phthalic acid diester at high temperature in the presence of a palladium compound-containing catalyst while supplying molecular oxygen to the reaction system requires no special equipment or complicated procedures, and constitutes an improved economical production process which allows effective utilization of the catalyst, easy control of the reaction and continuous production.

EXAMPLES

The process for production of biphenyltetracarboxylic acid tetraesters of the invention will now be explained in greater detail through reference examples and working examples. However, the invention is in no way limited to these examples.

Throughout the examples, dimethyl ester phthalate is used as the reaction starting material, and the yield of the biphenyltetracarboxylic acid tetramethyl ester (BPTT) oxidative dimerization product, the catalytic turnover number (TON) and the production ratio of the isomers 3,3',4,4'-biphenyltetracarboxylic acid tetramethyl ester (s-BPTT) and 2,3,3',4'-biphenyltetracarboxylic acid tetramethyl ester (a-BPTT) (hereinafter referred to as the S/A ratio) in the product were calculated by the following formulas. In the following formulae, the unit of the amounts of the components is mole.

Oxidative dimerization product yield (%)=2×(BPTT production per unit time)/(phthalic acid dimethyl ester supply per unit time)×100

TON=(BPTT production per unit time)/(palladium catalyst supply per unit time)

S/A=[s-BPTT/(s-BPTT+a-BPTT)×100]/[a-BPTT/(s-BPTT+a-BPTT)×100]

Reference Example 1
(Solubility of Palladium Compounds)

After adding 500 mg each of palladium acetate (hereinafter abbreviated as Pd(OAc)$_2$) and a complex of palladium acetate and 1,10-phenanthroline (hereinafter abbreviated as [(phen)Pd(OAc)$_2$]) to 5 ml of phthalic acid dimethyl ester, the mixture was stirred at 50° C. for 1 hour. It was then filtered with a 0.2 μm filter, and upon quantitating the remainder by inductively coupled plasma-atomic emission spectroscopy (ICP-AES) and calculating the solubility, the Pd(OAc)$_2$ exhibited a solubility of 12,000 μg (0.022-fold molar) in terms of metallic palladium with respect to 1 g of phthalic acid dimethyl ester and the [(phen)Pd(OAc)$_2$] exhibited a solubility of 510 μg (0.00093-fold molar) in terms of metallic palladium with respect to 1 g of phthalic acid dimethyl ester.

According to the invention, the palladium compound-containing catalyst preferably comprises the palladium compound, a bidentate ligand and a copper compound, and since it is the complex of the palladium compound and bidentate ligand which exhibits the actual catalytic activity, the palladium compound is preferably limited to no greater than 0.00093 mole with respect to one mole of the phthalic acid diester to allow not only the palladium compound but the complex of the palladium compound and the bidentate ligand, which exhibits the actual catalytic activity, to be supplied to the reactor as a homogeneously dissolved mixture.

Reference Example 2
(Solubility of Copper Compounds)

The solubilities of copper compounds in the phthalic acid dimethyl ester were measured. A 500 mg portion of each copper compound was added to 5 ml of phthalic acid dimethyl ester, and the mixture was stirred at 50° C. for 1 hour. It was then filtered with a 0.2 μm filter, and the remainder was quantitated by inductively coupled plasma-atomic emission spectroscopy (ICP-AES) and the solubility calculated, giving the following results.

Copper acetate monohydrate exhibited a solubility of 17 μg (0.000052-fold molar) in terms of metallic Cu with respect to 1 g of phthalic acid dimethyl ester, copper bis(acetylacetonate) exhibited 160 μg (0.00049-fold molar) in terms of metallic Cu with respect to 1 g of phthalic acid dimethyl ester, copper propionate monohydrate exhibited a solubility of 110 μg (0.00034-fold molar) in terms of metallic Cu with respect to 1 g of phthalic acid dimethyl ester, copper n-butyrate exhibited a solubility of 120 μg (0.00037-fold molar) in terms of metallic Cu with respect to 1 g of phthalic acid dimethyl ester, and copper isobutyrate exhibited a solubility of 31 μg (0.000094-fold molar) in terms of metallic Cu with respect to 1 g of phthalic acid dimethyl ester.

From these measurement results, it is seen that copper bis(acetylacetonate), copper propionate and copper n-butyrate are copper compounds which dissolve readily in phthalic acid diesters, and are therefore preferred for easier supply to the reactor as homogeneously dissolved mixtures in phthalic acid diesters.

Example 1

A reactor was used such as shown in FIG. 1, having a 50 ml glass reactor. Oxidative dimerization was conducted in the reactor while stirring with a stirrer, adjusting the internal temperature to 220° C., and bubbling A Grade air into the reaction mixture at 20 ml/min. A Grade air is dry air with a dew point of −80° C. or below.

Phthalic acid dimethyl ester was stirred with 0.00032 mole of palladium acetate, 0.00032 mole of 1,10-phenanthroline and 0.000096 mole of copper propionate monohydrate with respect to one mole of the phthalic acid dimethyl ester, at 80° C. for at least 30 minutes to homogeneous dissolution, the solution was supplied to the reactor by a liquid conveying pump while keeping the temperature at 80° C., and after the reaction mixture reached the prescribed volume, oxidative dimerization was conducted in a continuous operation while continuously extracting the reaction mixture in roughly the same amount as the supply of the starting mixture, using a liquid conveying pump at 10 ml/hour, so as to maintain an approximately constant liquid level in the reactor.

The extracted reaction mixture was cooled to room temperature and diluted with acetone, and then cholesterol acetate was added as an internal standard substance and each product of the reaction mixture extracted within 10–20 hours from the start of the reaction was quantitated by gas chromatography. The results are shown in Table 1.

The mean residence time of the reaction mixture in the reactor was 5 hours.

Example 2

The same procedure was conducted as in Example 1, except that the reaction mixture was continuously supplied to the reactor at 5 ml/hour. The results are shown in Table 1.

The mean residence time of the reaction mixture in the reactor was 10 hours.

Example 3

The same procedure was conducted as in Example 1, except that the internal temperature of the reactor was adjusted to 210° C. The results are shown in Table 1.

The mean residence time of the reaction mixture in the reactor was 5 hours.

Example 4

The same procedure was conducted as in Example 2, except that the internal temperature of the reactor was adjusted to 210° C. The results are shown in Table 1.

The mean residence time of the reaction mixture in the reactor was 10 hours.

Example 5

A reactor was used such as shown in FIG. 2, having two serially connected 50 ml glass reactors. Oxidative dimerization was conducted in both of the two reactors while stirring with a stirrer, adjusting the internal temperature to 220° C., and bubbling A Grade air into the reaction mixture at 20 ml/min.

Phthalic acid dimethyl ester was stirred with 0.00032 mole of palladium acetate, 0.00032 mole of 1,10-phenanthroline and 0.000096 mole of copper propionate monohydrate with respect to one mole of the phthalic acid dimethyl ester, at 80° C. for at least 30 minutes to homogeneous dissolution, the solution was supplied to the reactor by a liquid conveying pump while keeping the temperature at 80° C., and after the reaction mixture reached the prescribed volume, oxidative dimerization was conducted while continuously extracting the reaction mixture in roughly the same amount as the supply of the starting mixture, using a liquid conveying pump at 10 ml/hour, so as to maintain an approximately constant liquid level in the reactor, and supplying this to the second reactor.

After the reaction mixture reached the prescribed volume in the second reactor, oxidative dimerization was conducted in a continuous operation while continuously extracting the reaction mixture in roughly the same amount as the supply of the starting/reaction mixture, so as to maintain an approximately constant liquid level in the reactor.

The extracted reaction mixture was cooled to room temperature and diluted with acetone, and then cholesterol acetate was added as an internal standard substance and each product of the reaction mixture extracted within 10–20 hours from the start of the reaction was quantitated by gas chromatography. The results are shown in Table 1.

The mean residence time of the reaction mixture in the reactor was 10 hours.

Example 6

The same procedure was conducted as in Example 5, except that the reaction mixture was continuously supplied to the reactor at 5 ml/hour. The results are shown in Table 1.

The mean residence time of the reaction mixture in the reactor was 20 hours.

Example 7

The same procedure was conducted as in Example 5, except that the internal temperature of the reactor was adjusted to 210° C. The results are shown in Table 1.

The mean residence time of the reaction mixture in the reactor was 10 hours.

Example 8

The same procedure was conducted as in Example 6, except that the internal temperature of the reactor was adjusted to 210° C. The results are shown in Table 1.

The mean residence time of the reaction mixture in the reactor was 20 hours.

Comparative Example 1

The same procedure was conducted as in Example 1, except that the internal temperature of the reactor was adjusted to 250° C. The results are shown in Table 1.

The mean residence time of the reaction mixture in the reactor was 5 hours.

Comparative Example 2

The same procedure was conducted as in Example 5, except that the internal temperature of the reactor was adjusted to 250° C. The results are shown in Table 1.

The mean residence time of the reaction mixture in the reactor was 10 hours.

TABLE 1

|  | Reaction conditions | | | | Reaction results | | |
| --- | --- | --- | --- | --- | --- | --- | --- |
|  | No. of reactors | Starting material supply rate (ml/hr) | Mean residence time (hrs) | Reaction temperature (° C.) | Dimerization product yield (%) | TON | S/A |
| Example 1 | 1 | 10 | 5 | 220 | 7.8 | 122 | 93/7 |
| Example 2 | 1 | 5 | 10 | 220 | 8.3 | 129 | 93/7 |
| Example 3 | 1 | 10 | 5 | 210 | 5.6 | 88 | 91/9 |
| Example 4 | 1 | 5 | 10 | 210 | 7.1 | 111 | 89/11 |
| Example 5 | 2 | 10 | 10 | 220 | 10.0 | 156 | 93/7 |
| Example 6 | 2 | 5 | 20 | 220 | 10.1 | 158 | 93/7 |
| Example 7 | 2 | 10 | 10 | 210 | 8.9 | 139 | 91/9 |
| Example 8 | 2 | 5 | 20 | 210 | 9.7 | 152 | 90/10 |
| Comp. Ex. 1 | 1 | 10 | 5 | 250 | <1 | <15 | 87/13 |
| Comp. Ex. 2 | 2 | 10 | 10 | 250 | <1 | <15 | 87/13 |

Example 9

A reactor, as shown in FIG. 1 and having a 50 ml glass reactor, was used. Oxidative dimerization was conducted in the reactor while stirring with a stirrer, adjusting the internal temperature to 200° C., and bubbling A Grade air into the reaction mixture at 20 ml/min.

Phthalic acid dimethyl ester was stirred with 0.00032 mole of palladium acetate, 0.00032 mole of 2-pyridinecarboxylic acid, 0.00064 mole of trifluoroacetic acid and 0.000096 mole of copper propionate monohydrate with respect to one mole of the phthalic acid dimethyl ester, at 80° C. for at least 30 minutes to dissolution, the solution was supplied to the reactor by a liquid conveying pump while keeping the temperature at 80° C., and after the reaction mixture reached the prescribed volume, oxidative dimerization was conducted in a continuous operation while continuously extracting the reaction mixture in roughly the same amount as the supply of the starting mixture, using a liquid conveying pump at 10 ml/hour, so as to maintain an approximately constant liquid level in the reactor.

The extracted reaction mixture was cooled to room temperature and diluted with acetone, and then cholesterol acetate was added as an internal standard substance and each product of the reaction mixture extracted within 10–20 hours from the start of the reaction was quantitated by gas chromatography. The results are shown in Table 2.

The mean residence time of the reaction mixture in the reactor was 5 hours.

Example 10

The same procedure was conducted as in Example 9, except that the reaction mixture was continuously supplied to the reactor at 5 ml/hour. The results are shown in Table 2.

The mean residence time of the reaction mixture in the reactor was 10 hours.

TABLE 2

| | Reaction conditions | | | | Reaction results | | |
|---|---|---|---|---|---|---|---|
| | No. of re-actors | Starting material supply rate (ml/hr) | Mean residence time (hrs) | Reaction tempera-ture (° C.) | Dimeri-zation product yeild (%) | TON | S/A |
| Example 9 | 1 | 10 | 5 | 200 | 1.9 | 30 | 7/93 |
| Example 10 | 1 | 5 | 10 | 200 | 2.2 | 34 | 6/94 |

Example 11

A reactor as shown in FIG. 1 and having a 50 ml glass reactor, was used. Oxidative dimerization was conducted while stirring with a stirrer, adjusting the internal temperature (of the reaction mixture) to 220° C., and bubbling A Grade air into the reaction mixture at 20 ml/min. Phthalic acid dimethyl ester was stirred with 0.00032 mole of palladium acetate, 0.00032 mole of 1,10-phenanthroline, 0.000096 mole of copper propionate monohydrate and 0.00064 mole of acetic acid with respect to one mole of the phthalic acid dimethyl ester, at 80° C. for at least 30 minutes to homogeneous dissolution to prepare a starting mixture. The starting mixture was supplied to the reactor by a liquid conveying pump while keeping the temperature at 80° C., and after the reaction mixture reached the prescribed volume in the reactor, oxidative dimerization was conducted in a continuous operation while continuously extracting the reaction mixture in roughly the same amount as the supply of the starting mixture (10 ml/hour), using a liquid conveying pump, so as to maintain an approximately constant liquid level in the reactor. During the reaction, ejection of the acetic acid vapor out of the reaction system through the gas extraction conduit was confirmed by off-gas analysis based on gas chromatography with FID detector.

The extracted reaction mixture was cooled to room temperature and diluted with acetone and, then, cholesterol acetate was added as an internal standard substance and each product of the reaction mixture extracted within 10–20 hours and within 50–60 hours from the start of the reaction was quantitated by gas chromatography with FID detector. The results are shown in Table 3.

The mean residence time of the reaction mixture in the reactor was 5 hours.

Example 12

The same procedure was conducted as in Example 11, except that no acetic acid was added to the reaction mixture. Each product of the reaction mixture extracted within 10–20 hours and within 50–60 hours from the start of the reaction was quantitated. The results are shown in Table 3.

The mean residence time of the reaction mixture in the reactor was 5 hours. This example represents an extension of the reaction of Example 1.

Example 13

A reactor as shown in FIG. 2 and having two serially connected 50 ml glass reactors, was used. Oxidative dimerization was conducted in both of the two reactors while stirring with a stirrer, adjusting the internal temperature (of the reaction mixture) to 220° C., and bubbling A Grade air into the reaction mixture at 20 ml/min. Phthalic acid dimethyl ester was stirred with 0.00032 mole of palladium acetate, 0.00032 mole of 1,10-phenanthroline, 0.000096 mole of copper propionate monohydrate and 0.00064 mole of acetic acid with respect to one mole of the phthalic acid dimethyl ester, at 80° C. for at least 30 minutes to homogeneous dissolution to prepare a starting mixture. The reaction mixture was supplied to the first reactor by a liquid conveying pump while keeping the temperature at 80° C. and, after the starting/reaction mixture reached the prescribed volume in the reactor, oxidative dimerization was conducted in a continuous operation while continuously extracting the reaction mixture in roughly the same amount as the supply of the starting mixture (10 ml/hour) using a liquid conveying pump, so as to maintain an approximately constant liquid level in the reactor, and supplying this to the second reactor.

After the reaction mixture reached the prescribed volume in the second reactor as well, oxidative dimerization was conducted in a continuous operation while continuously extracting the reaction mixture in roughly the same amount as the supply of the reaction/starting mixture (10 ml/hour) using a liquid conveying pump, so as to maintain an approximately constant liquid level in the reactor. During the reaction, ejection of the acetic acid vapor out of the reaction system through the gas extraction conduit of the first and second reactors was confirmed by off-gas analysis based on gas chromatography with FID detector.

The extracted reaction mixture was cooled to room temperature and diluted with acetone, and then cholesterol acetate was added as an internal standard substance and each product of the reaction mixture extracted within 10–20 hours and within 50–60 hours from the start of the reaction was quantitated by gas chromatography with FID detector. The results are shown in Table 3.

The mean residence time of the reaction mixture in the reactor was 10 hours. This example represents an extension of the reaction of Example 5.

Example 14

The same procedure was conducted as in Example 13, except that no acetic acid was added to the starting mixture. Each product of the reaction mixture extracted within 10–20 hours and within 50–60 hours from the start of the reaction was quantitated. The results are shown in Table 3.

The mean residence time of the reaction mixture in the reactor was 10 hours.

TABLE 3-1

| Example | Starting material loading rate (ml/h) | Mean Resi-dence time (h) | Reactor levels | Reaction temperature | Acetic acid supply rate (with respect to one mole of Pd) |
|---|---|---|---|---|---|
| Example 11 | 10 | 5 | 1 | 220° C. | 2 moles |
| Example 12 | 10 | 5 | 1 | 220° C. | none |
| Example 13 | 10 | 10 | 2 | 220° C. | 2 moles |
| Example 14 | 10 | 10 | 2 | 220° C. | none |

TABLE 3-2

| Example | Oxidative dimerization reaction product (BPTT) yield (S/A) | | | |
| --- | --- | --- | --- | --- |
| | 10–20 hrs | TON | 50–60 hrs | TON |
| Example 11 | 8.3% (92/8) | 130 | 8.8% (93/7) | 138 |
| Example 12 | 7.8% (93/7) | 122 | 6.9% (93/7) | 108 |
| Example 13 | 10.7% (93/7) | 167 | 10.6% (93/7) | 166 |
| Example 14 | 10.0% (93/7) | 156 | 9.0% (93/7) | 141 |

What is claimed is:

1. A method for producing a biphenyltetra-carboxylic acid tetraester, comprising:
   providing a reaction mixture comprising a phthalic acid diester and a palladium compound-containing catalyst in a reactor,
   continuously or intermittently supplying a starting mixture to a portion of the reaction mixture in the reactor, wherein the starting mixture has been preliminarily prepared by mixing a phthalic acid diester and a palladium compound-containing catalyst outside the reactor, the palladium compound-containing catalyst being dissolved in said phthalic acid diester in the starting mixture,
   conducting an oxidative dimerization reaction of the phthalic acid diester in the presence of the palladium compound-containing catalyst at a temperature in a range of from 140° C. to less than 250° C. in the reactor while supplying molecular oxygen to the reaction mixture in the reactor, and
   continuously or intermittently removing a portion of the reaction mixture from the reactors,
   wherein the method is carried out in a continuous manner and the supplying, the reaction and the removing are carried out in parallel.

2. The method according to claim 1, wherein the starting mixture is kept at a temperature in the range of 50–100° C. before being supplied to the reactor.

3. The method according to claim 1, wherein the palladium compound-containing catalyst comprises a palladium compound, a bidentate ligand and a copper compound.

4. The method according to claim 1, wherein the amount of the palladium compound is no more than 0.00093 mole with respect to one mole of the phthalic acid diester.

5. The method according to claim 3, wherein the copper compound is selected from the group consisting of anhydrides or hydrates of copper propionate, copper n-butyrate, copper bis-(acetylacetonate) and copper pivalate.

6. The method according to claim 3, further comprising continuously or intermittently supplying a carboxylic acid to the reaction mixture in the reactor.

7. The method according to claim 6, wherein the carboxylic acid is selected from the group consisting of acetic acid, trifluoroacetic acid, propionic acid, pivalic acid and butyric acid.

8. The method according to claim 1, wherein the reactor comprises a plurality of serially connected reactors, the process comprising a step of continuously or intermittently supplying the starting mixture to a first reactor, a step of continuously or intermittently removing a portion of the reaction mixture from each reactor and successively introducing it into the next reactor, a step of conducting oxidative dimerization of the phthalic acid diester in a temperature range of from 140° C. and lower than 250° C. while supplying molecular oxygen to each reactor to form a reaction mixture and a step of continuously or intermittently removing out a portion of the reaction mixture from the final reactor,
   wherein the steps are carried out in parallel.

9. A method for producing a biphenyltetra-carboxylic acid ester, comprising
   employing a plurality of serially connected reactors including a first reactor and a second reactor,
   providing a reaction mixture comprising a phthalic acid diester and a palladium compound-containing catalyst in the first reactor,
   continuously or intermittently supplying a starting mixture to a portion of the reaction mixture in the first reactor, wherein the starting mixture has been preliminarily prepared by mixing a phthalic acid diester and a palladium compound-containing catalyst outside the first reactor, and the palladium compound-containing catalyst is dissolved in the phthalic acid diester in the starting mixture,
   conducting oxidative dimerization reaction of the phthalic acid diester in the presence of the palladium compound-containing catalyst at a temperature in a range of from 140° C. to lower than 250° C. in the first reactor while supplying molecular oxygen to the reaction mixture in the first reactor,
   continuously or intermittently removing a portion of the reaction mixture from the first reactor and introducing the removed portion of the reaction mixture in the second reactor,
   conducting oxidative dimerization reaction of the phthalic acid ester in the presence of the palladium compound-containing catalyst at a temperature in a range of from 140° C. to lower than 250° C. in the second reactor while supplying molecular oxygen to the reaction mixture in the second reactor,
   continuously or intermittently removing a portion of the reaction mixture from the second reactor, and
   repeating the same procedure as above for each reactor if present after the second reaction,
   wherein the production method is carried out in a continuous manner and the supplying, the reaction and the removing are carried out in parallel.

10. The method according to claim 9, wherein a carboxylic acid is also continuously or intermittently supplied to each of the reactors.

11. A method for producing a biphenyltetra-carboxylic acid tetraester, comprising producing a biphenyltetracarboxylic acid tetraester by oxidative dimerization reaction of a phthalic acid diester at high temperature while supplying molecular oxygen in the presence of a catalyst comprising a palladium compound, a bidentate ligand and a copper compound, wherein a carboxylic acid is further supplied continuously or intermittently.

12. The method according to claim 11, wherein the boiling point of the carboxylic acid is below the oxidative dimerization reaction temperature.

13. The method according to claim 11, wherein the carboxylic acid is selected from the group consisting of acetic acid, trifluoroacetic acid, propionic acid, pivalic acid and butyric acid.

* * * * *